US008895747B2

(12) United States Patent
Heindl et al.

(10) Patent No.: US 8,895,747 B2
(45) Date of Patent: Nov. 25, 2014

(54) METHOD AND SUBSTANCES FOR PREPARATION OF N-SUBSTITUTED PYRIDINIUM COMPOUNDS

(75) Inventors: Dieter Heindl, Paehl (DE); Heribert Maerz, Paehl (DE); Axel Schmidt, Tutzing (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 13/359,667

(22) Filed: Jan. 27, 2012

(65) Prior Publication Data

US 2012/0171730 A1 Jul. 5, 2012

Related U.S. Application Data

(63) Continuation of application No. PCT/EP2010/004522, filed on Jul. 23, 2010.

(30) Foreign Application Priority Data

Jul. 27, 2009 (EP) .................................... 09166455

(51) Int. Cl.
*C07D 213/78* (2006.01)
*C07D 213/79* (2006.01)
*C07D 213/82* (2006.01)
*C07D 213/83* (2006.01)
*C07D 401/04* (2006.01)
*C07D 473/04* (2006.01)
*C07D 473/16* (2006.01)

(52) U.S. Cl.
CPC ............ *C07D 401/04* (2013.01); *C07D 213/82* (2013.01); *C07D 473/16* (2013.01)
USPC ........ 546/256; 546/268.1; 544/194; 544/264; 544/253; 544/328

(58) Field of Classification Search
USPC ........ 546/256, 268.1; 544/194, 264, 253, 328
See application file for complete search history.

(56) References Cited

U.S. PATENT DOCUMENTS

| 4,411,995 | A | 10/1983 | Whitesides et al. | |
|---|---|---|---|---|
| 7,553,615 | B2 | 6/2009 | Heindl et al. | |
| 2008/0213809 | A1* | 9/2008 | Heindl et al. | 435/14 |
| 2009/0128882 | A1 | 5/2009 | Das et al. | |
| 2010/0210807 | A1 | 8/2010 | Hehn | |

FOREIGN PATENT DOCUMENTS

| DE | 102006035020 A1 | 2/2007 |
|---|---|---|
| EP | 2023418 A1 | 2/2009 |
| WO | 2007/012494 A1 | 2/2007 |
| WO | 2008/022966 A1 | 2/2008 |

OTHER PUBLICATIONS

International Search Report issued Jun. 28, 2011 in PCT Application No. PCT/EP2010/004522, 4 pages.
Bredereck, H. et al., "Über Pyridinium-pyrimidin- und Pyridinium-purin-betaine," Angewandte Chemie, 1960, p. 708, vol. 72.
Cheng, Wei-Chieh and Kurth, Mark J., "The Zincke Reaction. A Review," Organic Preparations and Procedures International, 2002, pp. 585-608, vol. 34, No. 6.
Cullum, Neil R. et al., "The aminolysis and hydrolysis of N-(4,6-diphenoxy-1,3,5-triazin-2-yl) substituted pyridinium salts: concerted displacement mechanism," Journal of the Chemical Society, Perkin Transactions 2, 1996, pp. 1559-1563.
Eda, Masahiro et al., "The Solid-Phase Zincke Reaction: Preparations of ω-Hydroxy Pyridinium Salts in the Search for CFTR Activation," Journal of Organic Chemistry, 2000, pp. 5131-5135, No. 65.
Goulioukina, Natasha et al., "Synthesis of Nicotinamide Adenine Dinucleotide (NAD) Analogues with a Sugar Modified Nicotinamide Moiety," Helvetica Chimica Acta, 2007, pp. 1266-1278, vol. 90.
Greene, Theodora W. and Wuts, Peter G.M., "Protective Groups in Organic Synthesis Third Edition," 1999, pp. 308-322, 725-727, John Wiley & Sons, Inc.
Hocková, Dana et al., "'Abbreviated' NAD+Analogues Containing a Phosphonate Function," Collection of Czechoslovak Chemical Communications, 1996, pp. 1538-1548, vol. 61.
Inagaki, Yoshio et al., "A new class of light-fast oxonol dyes: organic-glass forming salts of oxonol anions and 4,4'- bipyridinium cations," Journal of Materials Chemistry, 2006, pp. 345-347, vol. 16.
Kam, Bernard L. et al., "Pyridine Coenzyme Analogues. Synthesis and Characterization of α- and β-Nicotinamide Arabinoside Adenine Dinucleotides," Biochemistry, 1987, pp. 3453-3461, vol. 26.
Kam, Bernard L. and Oppenheimer, Norman J., "Synthesis of a new class of D-aldopentofuranosylamines, the 5-O-trityl-D-aldopentofuranosylamines," Carbohydrate Research, 1979, pp. 275-280, vol. 77.
Liu, Yi et al., "Palladium(II)-Directed Self-Assembly of Dynamic Donor-Acceptor [2]Catenanes," Organic Letters, 2008, pp. 765-768, vol. 10, No. 5.
Masternak, Anna et al., "Solvatochromism of a Novel Betaine Dye Derived from Purine," Journal of Physical Chemistry A, 2005, pp. 759-766, vol. 109.
Perrin, D. D., "Dissociation Constants of Organic Bases in Aqueous Solution," 1965, International Union of Pure and Applied Chemistry, Page Bros. Ltd., Norwich, Great Britain, 4 pages.
Sicsic, Sames et al., "Activity of NMN+, nicotinamide ribose and analoges in alcohol oxidation promoted by horse-liver alcohol dehydrogenase, Improvement of this activity and structural requirements of the pyridine nucleotide part of the NAD+ coenzyme," European Journal of Biochemistry, 1986, pp. 403-407, vol. 155.
Sugimoto, Tadaaki, "neutral-fixing reactive dyes for cotton. Part 2—commercial reactive dyestuffs and their classification," Journal of the Society of Dyers and Colourists, 1992, pp. 497-500, vol. 108.
Vianna, Gustavo H. R. et al., "Rapid Microwave-Promoted Solvent-Free Synthesis of Zincke's Salts and their Conversion into Chiral Pyridinium Salts in Water," Letters in Organic Chemistry, 2008, pp. 396-398, vol. 5.
Walt, David R. et al., "An Efficient Chemical and Enzymatic Synthesis of Nicotinamide Adenine Dinucleotide (NAD+)," Journal of the American Chemical Society, 1984, pp. 234-239, vol. 106.
Werner, D. and Hoffmann, H., "Puryl-6-ammonium- and imonium-Derivatives as Substrates for Xanthine Oxidase," H. Archiv der Pharmazie, 1974, pp. 301-308, vol. 307.

* cited by examiner

*Primary Examiner* — Venkataraman Balasubramanian
(74) *Attorney, Agent, or Firm* — Faegre Baker Daniels LLP

(57) ABSTRACT

Methods for the synthesis of N-substituted pyridinium compounds by using an N-heteroaryl substituted pyridinium salt (Zincke salt) and reacting it with a nucleophilic amine are provided. Novel purine-substituted pyridyl compounds, which may be useful reagents in the above reaction, are also disclosed.

12 Claims, No Drawings

US 8,895,747 B2

METHOD AND SUBSTANCES FOR PREPARATION OF N-SUBSTITUTED PYRIDINIUM COMPOUNDS

RELATED APPLICATIONS

This application is a continuation of International Application No. PCT/EP2010/004522, filed Jul. 23, 2010, which claims the benefit of European Patent Application No. 09166455.7, filed Jul. 27, 2009, the disclosures of which are hereby incorporated by reference in their entirety.

BACKGROUND

1. Technical Field

The present disclosure relates to methods for the synthesis of N-substituted pyridinium compounds. The present disclosure also relates to novel purine-substituted pyridyl compounds which can be used in the methods and reactions disclosed herein.

2. Description of the Related Art

Pyridinium compounds are of interest in, for example, drug design and as general intermediates for organic syntheses, such as in natural product synthesis. Certain substituted pyridinium compounds are useful in the synthesis of NAD or NAD analogs, respectively. Additionally, certain heteroaryl substituted pyridinium compounds have been studied in relation to solvatochromism.

Triazinyl reactive dyes having carboxypyridine as a leaving group are known as useful in the coloration of cotton. In the coloration procedure, the pyridinium moiety acts as a leaving group when a triazinyl dye is reacted with nucleophiles. Fixation of the dye would not occur, however, if pyridinium ring opening (as in the Zincke-like pathway described herein) occurred.

Zincke salts may be prepared by reacting a pyridinium compound with 2,4 dinitro halobenzol, for example with 2,4 dinitrochlorbenzol and 2,4 dinitrobrombenzol.

Currently, the standard method for the synthetic production of substituted pyridinium compounds includes alkylation of pyridine derivatives. However, this reaction is only convenient when using primary alkyl halides. When secondary or tertiary alkyl halides are used, elimination occurs as an unwanted side reaction and yields are generally low. Moreover, when the alkylation is performed with alkyl halides having a halogen atom attached to an asymmetric carbon atom, racemization may occur during the nucleophilic displacement reaction.

As is apparent from the above description, the presently used activation reagents in the production of substituted pyridinium compounds are toxic, explosive, and/or otherwise hazardous, and are therefore limited to small scale research applications. Additionally, while there were sporadic attempts at performing Zincke reactions in an ecofriendly manner, for example by using microwave assisted synthesis, such attempts still rely on explosive dinitrophenyl compounds and are not capable of being scaled up without taking expensive precautionary measures.

As such, there is a need for an improved method for synthesis of N-substituted pyridinium compounds which avoids hazardous activation reagents and other problems known in the art.

SUMMARY OF THE DISCLOSURE

The present disclosure relates to a method of synthesizing N-substituted pyridinium compounds with novel, less hazardous activation reagents allowing for safer production procedures and for easier, less risky, and more efficient production of such compounds at much larger scales.

According to an embodiment of the present disclosure, N-substituted pyridinium compounds are synthesized by reacting an N-heteroaryl substituted pyridinium salt (Zincke salt) with a nucleophilic amine. According to such embodiments, the pyridinium ring of the Zincke salt reacts with the amine which induces ring opening followed by ring closing, whereby the nitrogen of the amine becomes part of the N-substituted pyridinium ring. In particular embodiments, the amine comprises a primary amine. According to some embodiments of the instant disclosure, novel purine-substituted pyridyl compounds may be used in the above reaction.

As described in further detail herein, the limitations and deficiencies of prior methods for the synthetic production of substituted pyridinium compounds, such as described above, may be overcome by using a Zincke reaction of the instant disclosure. According to embodiments of the instant disclosure, the Zincke reaction includes the reaction of Zincke salts with alkyl or aryl amines. Zincke salts comprise activated pyridinium salts capable of reacting with a primary amine (R—NH2). According to some embodiments, ring opening is induced, followed by ring closure, to produce an R-substituted pyridinium compound. Embodiments of the instant disclosure may also be performed with hydrazines, hydroxylamine, and carboxylic or sulfonic acid hydrazides. Embodiments of the "Zincke reactions" disclosed herein may be suitable for in-solution synthesis and/or for solid phase organic synthesis, for example.

According to an embodiment of the instant disclosure, pyridinium compounds may be reacted with appropriate aromatic heterocycles, thereby forming a Zincke-type salt. The heteroaryl-substituted pyridinium salts of the instant disclosure, are surprisingly useful for reacting with primary amine nucleophiles, in Zincke-type reactions for example. Unexpectedly, the formation of the Zincke salt, and the Zincke reaction of primary amines with N-heteroaryl pyridinium compounds, both result in high yields. Additionally, as disclosed herein, both the Zincke salt formation as well as the Zincke reaction can be performed under less vigorous reaction conditions as compared to current state of the art procedures and can be easily scaled up. As is further disclosed herein, after the Zincke reaction is completed, the heteroaryl byproduct of the Zincke-type reaction usually exhibits low solubility and precipitates. Therefore, it can be easily separated from the reaction mixture, which aids the isolation of the N-substituted pyridinium compound.

Based on the unexpected findings presented herein, many of the problems known from the art can be avoided and overcome.

One embodiment of the present disclosure relates to a method for synthesis of an N-substituted pyridinium compound comprising the steps of providing a N-heteroaryl substituted pyridinium salt (Zincke salt), reacting the Zincke salt with an amine (R—NH2) under appropriate conditions, thereby obtaining/recovering an N-substituted pyridinium compound substituted with the R residue of the primary amine.

Embodiments of the instant disclosure also relate to novel Zincke-type salts. These Zincke-type salts can be used, for example, in the synthesis of N-substituted pyridinium compounds.

Furthermore, according to the instant disclosure, certain substituted pyridinium compounds, produced according to methods as presently disclosed, are of great utility in the synthesis of NAD or NAD analogs such as carba-NAD.

DETAILED DESCRIPTION

The embodiments disclosed herein are not intended to be exhaustive or limit the disclosure to the precise form disclosed in the following detailed description. Rather, the embodiments are chosen and described so that others skilled in the art may utilize their teachings.

An embodiment of the present disclosure relates to a method for synthesis of an N-substituted pyridinium compound comprising the steps of providing a N-heteroaryl substituted pyridinium salt (Zincke salt), reacting the provided Zincke salt with a primary amine (R—NH2) under appropriate conditions and obtaining/recovering an N-substituted pyridinium compound substituted with the R residue of the primary amine.

According to the instant disclosure, Zincke-type salts may be prepared by reacting pyridines with electron deficient heteroaromates which are substituted with a leaving group.

An "electron deficient heteroaromate" or "electron poor heteroaromate," according to the instant disclosure, comprises a 6-membered heteroaromate including an unsaturated aromatic ring system with a minimum of two sp2 N atoms which are in ortho or para position to a leaving group.

A "leaving group" comprises an appropriate group that is attached to the reactive center of the 6-membered unsaturated aromatic ring system. The reactive center carrying the leaving group comprises an sp2 carbon atom which is adjacent to a sp2 nitrogen atom (in ortho position to an sp2 N).

A "Zincke salt" or "Zincke-type salt" comprises a pyridinium compound which bears an electron withdrawing moiety at the nitrogen atom of the pyridinium ring. In Zincke-type salts, according to the present disclosure, the electron withdrawing group comprises an electron deficient heteroaromatic moiety.

An "electron deficient heteroaromatic moiety" or "electron poor heteroaromatic moiety," according to this disclosure, comprises a 6-membered heteroaromatic moiety characterized by an unsaturated aromatic ring system with a minimum of two sp2 N atoms which are in ortho or para position to the pyridinium ring of the Zincke type salt.

The term "Zincke reaction" or "Zincke-type reaction" relates to the reaction of a Zincke salt with an amine nucleophile, as described herein, in the formation of an N-substituted pyridinium compound.

As should be understood, the heteroaromatic compound comprises an electron deficient heteroaromate carrying a substituent which acts as a leaving group. The electron deficiency of the aromatic heterocycle favors nucleophilic substitution reactions and allows for reaction with pyridines, i.e. for the formation of a Zincke salt.

In order to allow for a reaction under non vigorous conditions, e.g. avoiding very high temperature, and in order to avoid non scalable methods like microwave synthesis, the reaction center, i.e. the atom to which the leaving group is bound must be activated in such a way that the reaction with pyridines performs quite easily. Activation of the leaving group is achieved by choosing heterocycles which have in ortho and para position to the leaving group an sp2 nitrogen atom, since in this case the reactive center where the nucleophilic attack of the pyridine nitrogen atom occurs is more positively charged.

Such N-heteroaryl substituted pyridinium compounds are in principle capable of two reaction pathways when reacted with amine nucleophiles: ring opening of the pyridinium moiety, or nucleophilic displacement wherein the pyridinium moiety acts as a leaving group. Therefore the extent of activation of the leaving group must be well balanced. The present investigators found that especially useful heteroaryl moieties include purines and substituted triazines. The substituents on the purine or triazine carbon atoms are chosen in such a manner that reactivity towards pyridinium nucleophiles is high enough so that the ring open/ring closure pathway is preferred over nucleophilic displacement. Another important role is that solubility in a given solvent is directed in such a manner that the amine-substituted purine or triazine, which is the result of the Zincke reaction, precipitates and therefore is easy to separate from the desired N-substituted pyridinium compound, preferably by filtration. For large scale synthesis the costs of materials, for example the heterocycle used, are a further selection criterion. It is apparent to the skilled artisan that for different pyridine compounds, different combinations with heterocycles and different solvents may be more suitable.

According to one embodiment of the present disclosure, a Zincke-type salt is generated by reaction of an electron-deficient aromatic heterocycle having an unsaturated aromatic ring system with a minimum of two sp2 N atoms which are in ortho or para position to a substituent acting as a leaving group, with a pyridine of interest. In this reaction a Zincke-type salt according to Formula I is formed.

A Zincke-type salt consists of the positively charged heteroaryl substituted pyridinium moiety as depicted in Formula I and a suitable counter ion.

Examples of heteroaromates useful in the generation of Zincke salts include chlorotriazines, 6-chloro-purines, 4-chloro-pyrimidines and 4-chloro-quinazolines. The 6-membered heteroaromatic ring may be substituted on the sp2 carbon atoms, with the exception of the sp2 carbon atom of the reactive center, with substituents independently selected from amino, alkyl amino, aryl amino, alkoxy, hydroxyl, alkyl, aryl and halogen, or two adjacent sp2 carbon atoms can be members of a further aromatic or heteroaromatic ring, like in purines or quinazolines. These heteroaromates also represent suitable heteroaromates for use in synthesis of a Zincke salt and thereby in a subsequent Zincke-type reaction according to the present disclosure.

As mentioned above, the electron deficient heteroaromate carries a leaving group. Specific suitable leaving groups are Cl, Br, 4-methylphenyl-sulfonyloxy, trifluormethyl-sulfonyloxy, and methyl-sulfonyloxy. In very specific embodiments Cl is used as a leaving group.

The counter ion is determined by the leaving group. Appropriate and specific counter ions include chloride, bromide, tosylate, mesylate and triflate. In some reactions it is useful to exchange the counter ion with a non-nucleophilic counter ion like dodecyl sulfate or tetrafluoroborate.

One embodiment of the present disclosure relates to a method for synthesis of an N-substituted pyridinium compound comprising the steps of:

(a) providing a Zincke salt according to Formula I:
Formula I

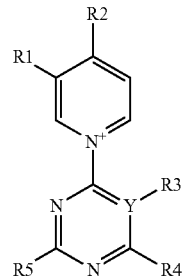

having a counter ion, wherein R1 is selected from H, alkyl, aryl, 2-methyl-1,3-dioxolan-2-yl, aryloxy, alkyloxy, hydroxyalkyl, arylalkyl, N-protected aminoalkyl, alkenyl, alkinyl, arylalkenyl, arylalkinyl C=XNH2, C=XNHalkyl, C=XN(alkyl)2C=XNHaryl, C=XN(aryl)2, C=Xaryl, C=X alkyl, COO alkyl, wherein R2 is selected from H, alkyl, aryl, pyrid-4-yl, alkylpyridinium-4-yl, 2-methyl-1,3-dioxolan-2-yl, aryloxy, alkyloxy, hydroxyalkyl, arylalkyl, protected amino alkyl, alkenyl, alkinyl, arylalkenyl, arylalkinyl, C=XNH2, C=XNHalkyl, C=XN(alkyl)2, C=XNHaryl, C=XN(aryl)$_2$, C=Xaryl, C=Xalkyl, COOalkyl, alkylsulfanyl,

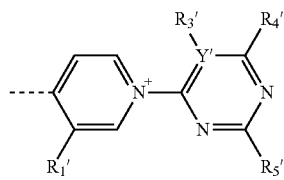

wherein at least one of R1 or R2 is H or alkyl or the residues R1 and R2 together are a butan-1,4-diyl, or a butadiene-1,4-diyl moiety linked to each other forming a 6-membered cycle, wherein independently in R1 or R2 alkyl is linear or branched C1-C6 alkyl or C5-C6 cycloalkyl, alkenyl is linear or branched C2-C6 alkenyl, alkinyl is linear or branched C2-C6 alkinyl and aryl is phenyl or naphthyl, wherein X=S or O, wherein Y is N or C; in case Y is N no R3 is present and in case Y is C, then R3 is H, C1-C3 alkyl, or forming together with R4 and the two sp2 carbon atoms to which R3 and R4 are attached a 5- or 6-membered aromatic ring system, optionally comprising 1 or 2 nitrogen atoms, wherein R4 is H, C1-C3 alkyl, hydroxy, O—C1-C3 alkyl, amino, C1-C3 alkyl-amino, phenylamino, phenyl or forming together with R3 and the two sp2 carbon atoms to which R3 and R4 are attached a 5 or 6-membered aromatic ring system, optionally comprising 1 or 2 nitrogen atoms, wherein R5 is H, C1-C3 alkyl, hydroxy, O—C1-C3 alkyl, amino, C1-C3 alkyl-amino, phenylamino, phenyl or halogen, and wherein each of Y', R1', R3', R4' and R5', in case Formula I represents a bipyridyl compound, are the same as the corresponding Y, R1, R3, R4 and R5;

(b) reacting the Zincke salt of step (a) with a primary amine of Formula II:

Formula II

wherein R6 is part of a primary organic amine comprising an sp2 or an sp3 carbon atom which is bound to the —NH$_2$ moiety, or R6 is a residue which together with —NH$_2$ is a hydrazine, a hydroxylamine, a sulfonyl hydrazide or a carbohydrazide; and wherein R6 is part of a primary organic amine comprising an sp2 or an sp3 carbon atom which is bound to the —NH2 moiety, or R6 is a residue which together with —NH2 is a hydrazine, a hydroxylamine, a sulfonyl hydrazide or a carbohydrazide; and (c) thereby obtaining/recovering an N-substituted pyridinium compound of Formula III:

Formula III

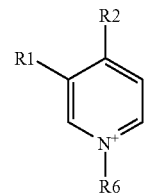

having a counter ion, and wherein R1, R2, and R6 are as defined above (in regard to Formulas I and II).

A range of appropriate reaction conditions is e.g. described and illustrated by means of the Examples given.

In a specific embodiment, in R1 or R2, independently of each other, alkyl is linear or branched C1-C6 alkyl or C5-C6 cyclo alkyl, alkenyl is linear or branched C2-C6 alkenyl, alkinyl is linear or branched C2-C6 alkinyl and aryl is phenyl or naphthyl.

Examples of a pyridinium moiety in a Zincke-type salt for use in a method according to the present disclosure include a) para-substituted pyridines like pyrid-4-yl, alkylpyridinium-4-yl, 2-methyl-1,3-dioxolan-2-yl, C=ONH2, C=ONEt2, COOalkyl, naphthyl, phenyl, anthracen-9-yl, 2-(9-anthracenyl)ethenyl, methyl, propyl, t.-butyl, N-trifluoracetyl-2-amino-ethyl, 3-hydroxypropyl, methylsulfanyl, or "dimeric Zincke" salts resulting from reacting bipyridines on both N atoms with an electron deficient heterocycle; b) meta-substituted pyridines carrying substituents like phenyl, methyl, C=ONH2, C=ONEt2[(methoxyimino)methyl]-, COOEt, methoxy, (β-hydroxytridecyl)-, [(9E)-12-N boc-amino]-9-dodecen-1-yl], hydroxymethyl, (2-methyl-1,3-dioxolan-2-yl)-; c) pyridines having para and meta substituents, e.g. with R1 and R2 being methyl or forming together a ring, e.g. the Isoquinolinium-Zincke salts and derivatives thereof, e.g. the 8-methyl or 6,7-dimethoxy isoquinolinium derivatives.

In some embodiments the para and meta substituents are linked to each other, thereby together with the pyridinium ring forming an isoquinolinium ring or a derivative thereof.

In one specific embodiment the pyridine moiety used in a method according to the present disclosure does not fall into the definition of Formula I but has two methyl groups in meta position.

In other specific embodiments either R1 or R2 of Formula I is selected from phenyl, CONH2, CSNH2, carboxy-(C1-C6)-alkyl, (C1-C6)-alkyl and 2-methyl-1,3-dioxolan-2-yl. More specifically, either R1 or R2 is CONH2 or CSNH2 and the other is hydrogen, respectively, and further specifically, R1 is CONH2 and R2 is H.

In one embodiment the pyridinium ring according to Formula I bears only one substituent in the meta position. The substituent in meta position is selected from C=ONH2, C=SNH2, C=OCH3,2-methyl-1,3-dioxolan-2-yl, (C1-C6)-alkyl or phenyl.

In some embodiments of the synthesis of the N-substituted pyridinium compound a Zincke-type salt according to Formula I is used wherein Y is N and both R4 and R5 are alkoxy each independently with a C1 to C3 alkyl group. In specific embodiments, the Zincke-type salt is based on 2-chloro-4,6-dimethoxy-triazine, and 2-chloro-4,6-diamino-triazine. As the skilled artisan will appreciate also an N-substituted derivative thereof (e.g. a simazine, atrazine, anilazine, propazine) can be used in a method according to the present disclosure.

In another embodiment of a method according to the present disclosure a Zincke-type salt according to Formula I is used wherein X is C, i.e. it is based on an appropriate pyrimidine. In one embodiment both R3 and R4 are hydrogen or C1 to C3 alkyl and R5 is NH2 or N-dialkyl (C1 to C3). Other suitable pyrimidines for use in the production of a Zincke-type salt in accordance with the methods are selected from the group consisting of 6-chloro-2,4-dimethoxypyrimidine, 2,4-dichloropyrimidine, 4 chloro-2,6-diaminopyrimidine, 4-amino-2,6-dichloropyrimidine, 4-chloro-2,6-dimethylpyrimidine and 2-amino-4-chloro-pyrimidines.

In a further specific embodiment in a method according to the present disclosure a Zincke-type salt according to Formula I is used wherein X is C and R3 and R4 form an aromatic cycle.

According to another embodiment, a Zincke-type salt according to Formula I is used wherein Y is C and R3 and R4 are linked to each other to form together with the sp2 carbon atoms to which R3 and R4 are attached an imidazole ring, i.e. in this case the Zincke salt is based on a purine ring system. In specific embodiments, the Zincke-type salt used in a method according to the present disclosure is based on activation of a purine or substituted purine, for example, 6-chloro purine, 2-amino-6-chloro purine or 2,6 dichloro purine are used.

In accordance with other embodiments, a Zincke-type salt according to Formula I is used wherein Y is C, and R3 and R4 are linked to each other to form together with the sp2 carbon atoms to which R3 and R4 are attached an aromatic 6-membered ring system, i.e. in this case the Zincke salt is based on a quinazoline ring system. Quinazolines suitable for use in a method according to the present disclosure include 2,4-dichloro-6,7-dimethoxyquinazoline and 4-chloro-6,7-dimethoxy-quinazoline.

Due to environmental impact concerns, a Zincke-type salt bearing only one halogen atom may be selected in order to avoid halogenated organic waste.

The present disclosure further relates to a Zincke-type salt selected from the group consisting of compounds as defined by Formulas IV, V, VI and VII (provided below).

Formula IV wherein,
  X is O or S,
  R1 is methyl, ethyl, O-methyl, O-ethyl, NH2, N-dimethyl, N-diethyl, and
  R2 is NH2.

Formula V wherein,
  X is O or S,
  R1 is methyl, ethyl, O-methyl, O-ethyl, NH2, N-dimethyl, N-diethyl, and
  R2 is NH2 or Cl.

Formula VI wherein,
  X is O or S,
  R1 is methyl, ethyl, O-methyl, O-ethyl, NH2, N-dimethyl, N-diethyl, and
  R2 and R3 independently are O—C1-C3 alkyl or NH2.

Formula VII wherein,
  X is O or S,
  R1 is methyl, ethyl, O-methyl, O-ethyl, NH2, N-dimethyl, N-diethyl, and
  R2 and R3 independently are O—C1-C3 alkyl and R7=H or Cl.

In one embodiment the present disclosure relates to a Zincke-type salt according to Formula IV.

In a specific embodiment the present disclosure relates to a Zincke-type salt according to Formula V.

In another specific embodiment the present disclosure relates to a Zincke-type salt according to Formula VI.

In still another specific embodiment the present disclosure relates to a Zincke-type salt according to Formula VII.

More generally, a Zincke-type salt according to Formula IV, V, VI or VII is used.

In accordance with some embodiments, a Zincke-type salt according to Formula I is used wherein R1 is hydrogen and R2 is CONH2. If such Zincke-type salt is used the synthesis method according to the present disclosure leads to an N-substituted nicotinamide derivative. In the generation of substituted nicotinamide, Zincke-type salts based on 2-amino-6-chloro-purine, 2-amino-4-chloropyrimidine, 4-chloro-6,7-dimethoxquinazoline or 2-chloro-4,6-dimethoxy triazine may be used.

In one specific embodiment according to the present disclosure a 6-chloro purine is reacted with a pyridinium compound and the resulting 1-(purin-6-yl)-pyridinium salt is reacted with a primary amine.

In another specific embodiment nicotine amide is reacted with 2-amino-6-chloro-purine to produce the Zincke salt 1-(2 amino-purin-6-yl) 3 carboxamidopyridinium chloride and subsequent this Zincke salt is reacted with a primary amine.

As mentioned above the Zincke reaction can be performed with any appropriate nucleophilic amine (R—NH2). The nature of R in the amine R—NH2 can be very broad. As the skilled artisan will appreciate R will be selected in such a manner that the amino group attached to it has a nucleophilicity that is high enough to attack the C2 or C6 carbon atom of the pyridinium moiety of a Zincke salt in a method according to the present disclosure.

Even though the empirical concepts of basicity and nucleophilicity are related but not strictly proportional, chemists use pKa values for obtaining at least a rough insight into the relative reactivity of amines (see e.g. Jaramillo, P. et al., Journal of Physical Organic Chemistry 20 (2007) 1050-1057).

pKa values are known for a plurality of amines (cf.: Dissociation Constants of Organic Bases in Aqueous Solution, (Pure and Applied Chemistry), Perrin, D. D., London (1965) pp. 473).

Accordingly, one embodiment provides that the amine R—NH2 has a pKa-value of from 1.7 (inclusive) to 12 (inclusive).

R is chosen such that the amine is a primary amine as defined in Formula II (R6-NH2). Appropriate selection of the primary amine R6-NH2 for use in a method according to the present disclosure makes it possible to generate the desired pyridinium compound with an R6-substituted nitrogen.

Typically primary alkyl amines have an pKa from 10-11. Primary alkyl amines (R6-NH2) having an sp3 carbon atom in R6 bound to the amino group represent a specific embodiment according to the present disclosure.

In case the primary amine R6-NH2 has an sp2 carbon atom in R6 bound to the amino group, the nucleophilicity of such primary amine can easily be evaluated by comparison to a reference compound.

In one embodiment according to the present disclosure the pKa-value for the arylic or heteroarylic amine R6-NH2, the latter not comprising a basic ring nitrogen atom, is the same as determined for 4-cyano aniline or it is above the pKa as measured for this compound. pKa value determination by titration is a well established method and automated tritrators specialized on pKa measurements are commercially available. In a specific embodiment the pKa is determined with Sirius T3 according to the instructions provided by the manufacturer (Sirius Analytical Ltd. Riverside, East Sussex, UK).

For amino substituted nitrogen heterocycles with a ring nitrogen atom, the ring nitrogen atom being the most basic site, direct measurement of the basicitiy of the exocyclic amino group is not possible. In this case the procedure as described in Deady, L. W. et al., Aust. J. Chem 37 (1984) 1625-1630, the entire disclosure of which is incorporated herein by this reference, has to be applied. In case the heteroarylamine is an amino substituted nitrogen heterocycle with a basic ring nitrogen atom the pKa preferably is the same as determined for 4 amino pyridine or it is above the pKa as measured for this compound.

In one embodiment R6 is part of a primary organic amine comprising an sp2 or an sp3 carbon atom which is bound to the —NH2 moiety, or R6 is a residue that together with —NH2 is a hydrazine, a hydroxylamine, a sulfonyl hydrazide or a carbohydrazide.

In some embodiments R6 together with —NH2 is a primary organic amine, or R6 is selected from the group consisting of —OH, —NH2, —N(C1-C6alkyl)2, —NHC=Oaryl, —NHSO2aryl, —NHSO2-(C1-C6)alkyl, —NHC=O(C4-C13)-heteroaryl comprising one optionally substituted heteroatom selected from N, O, S or N—(C1-C6)-alkyl or protected N, —NHSO2, C4-C13-heteroaryl comprising one substituted heteroatom selected from N, O, S or N—C1-C alkyl or protected N, wherein N is protected by a tosyl- or boc-protecting group.

A primary organic amine is an amino group that is bound via a single valency bond to an sp3 or to an sp2 carbon atom.

In case R6 is part of a primary organic amine comprising an sp2 or an sp3 carbon atom which is bound to the —NH2 moiety, the sp2 carbon atom preferably is part of an aromatic or a heteroaromatic moiety, or the sp3 carbon atom preferably is part of a carboacyclic moiety, a heteroacyclic moiety, a carbocyclic or a heterocyclic moiety.

In one embodiment either R6 is selected from the group consisting of alkyl, alkenyl, alkinyl, heterocycloalkyl, aryl, heteroaryl, or Formula II represents an amino alcohol, an amino acid, a furanosylamine or a cyclopentylamine.

As the skilled artisan will appreciate even compounds having an additional principally nucleophilic group in R6 can be used. In this case the further nucleophilic group has to be protected by an appropriate protecting group. Protecting groups are well known from the art and reviewed in standard text books (for example, see Greene, T., Protective groups in organic synthesis, John Wiley&Sons, Inc. (1981) New York, Chichester, Brisbane, Toronto). For example, amino groups, e.g. in N-protected alkyl, are protected by tosyl-, boc-, phthaloyl- or trifluoracetyl-protecting groups. Mercapto groups may be protected as disulfide.

R6 alkyl may comprise a linear or branched (C1-C20)-alkyl or a mono-, bi- or tricyclo (C3-C10)-alkyl; a linear or branched (C3-C20)alkenyl or a mono-, bi- or tricyclo (C5-C10)-alken-1-yl with the amino group attached to an sp3 carbon atom; linear or branched (C3-C20)-alkinyl with the amino group attached to an sp3 carbon atom; (C5-C6)-cycloalkyl comprising one optionally substituted heteroatom selected from O, NC1-C3 alkyl, protected N; a C6-C14 aryl moiety; a C4-C13 heteroaryl moiety comprising one optionally substituted heteroatom selected from N, O, S or N—C1-C6 alkyl or protected N. The nomenclature C4 to C13 relates to heteroaryl rings with a total number of 5 to 14 ring atoms of which one is a hetero atom as mentioned above.

For amines derived from alkylalkenyl, cycloalkenyl, cycloalkanyl, polycycloalkan, or heterocycloalkanes the following selected examples represent specific embodiments for a primary organic amine according to Formula II and its use in a method according to the present disclosure:

a) alkyl and alkenyl amines are selected from the group consisting of (S)-Phenylalaminol, D-Phenylethylamine, 4-Pyridinemethanamine, Propylamine, 2-Amino-1-phenyl-1,3-propanediol, 3-Pyridinetridecanamine, (3-Vinyl-4-isopropoxybenzyl)amine, 2-Phenylglycine, Serine, Isoleucin, beta-Alanyl-L-Histidine, 9-(3-Pyridinyl)-, 3-nonen-1-amine, 6-Amino-beta-(aminomethyl)-9H-purine-9-butanol and p-(Aminomethyl)benzenesulfonamide;

b) cycloalkene is (1R,4S,6S)-4-amino-6-hydroxy-2-Cyclohexene-1-methanol-1-(dihydrogen phosphate), c) cycloalkane is cyclohexylamine, trans-2-Phenylcyclopropylamine, or (1S,2R,3S,5S)-3-Amino-5-(hydroxymethyl)-1,2-Cyclopentanediol, d) polycycloalkane is tricyclo[3.3.1.13.7]decan-1-amine and e) heterocycloalkane is selected from 4-Amino-3-methyl-1-(phenylmethyl)-3-Piperidinol, (2S)-2-Aminomethylpyrrolidine-1-carboxylic acid tert-butyl ester; 2-Amino-1,5-anhydro-2-deoxy-6-(dihydrogen phosphate) D-altritol; 2-Amino-1,5-anhydro-2,3-dideoxy-, and 6-(dihydrogen phosphate) D-arabino-hexitol.

Where R6 represents an aryl moiety the corresponding arylamine according to Formula II is selected from 4-Aminobenzonitrile, 2-Hydroxy-4-aminobenzoic acid; p-Hexadecylaniline, 2,5-Dimethylaniline; p-Phenylenediamine, 1,4-Diamino-2,5-dimethylbenzene, 4-Halogenoaniline; 3-Bromo-4-isopropoxyaniline, 4-Isopropoxy-3-vinylaniline, 1-Naphthylamine, 4-(Aminobenzyl)phosphonic acid diethyl ester; p-Aminophenol; p-Aminobenzyl alcohol, 4-(Pyridin-4-ylmethyl)phenylamine; 4-Aminophenylsulfonic acid, 4-Aminobenzoic acid; 4-(Acetylamino)aniline; Dimethyl-5-aminoisophthalate; p-Aminoacetophenone; 2,2-dimethyl-1,3-Benzodioxol-5-amine.

Where R6 is a heteroaryl moiety, i.e. the compound according to Formula II is a heteroaryl, the compound according to Formula II is selected from the group consisting of 6-aminoquinoline, 4-amino-pyridine and 3-amino-pyridine.

In some embodiments the primary amine used in a method according to the present disclosure is a pure enantiomeric primary amine wherein the amino group is attached to a stereocenter. This is preferred where stereospecific production of the pyridinium compound is desired.

As the skilled artisan appreciates such primary amines can comprise further substituents which do not interfere with the Zincke reaction or are unstable under conditions of the Zincke reaction. In one embodiment the compound according to Formula II used in a method according to the present disclosure is a substituted alkyl amine.

Specific compounds according to Formula II for use in a method according to the present disclosure are pure stereoisomers of amino alcohols and amino acids.

An amino alcohol may be derived from any naturally occurring or any commercially available non-natural amino acid. In specific embodiments the amino alcohol is selected from the group consisting of serinol, threoninol, phenylalaminol, 2,5 diamino 1-Pentanol, (from ornithin) 2,6 diamino-1-hexanol (from lysine).

Where the compound according to Formula II is an amino acid, the amino acid may be selected from any naturally occurring or any commercially available non-natural amino acid. In specific embodiments the amino acid either is a naturally occurring amino acid or a non-naturally occurring amino acid. In very specific embodiments the compound according to Formula II is an amino acid selected from serine, threonine, phenylalanine, ornithin, lysine, and leucine.

If desired, in a further alternative embodiment di- or polyamines where no amino group is protected can be reacted with two or more equivalents of Zincke type salts, in order to form di-pyridinium or poly-pyridinium compounds.

Other suitable primary amines are amines substituted with furanosyl sugar moieties or analogs of such furanosyl sugar moieties, which optionally are phosphorylated at an OH group or compromise protected hydroxyl groups, whereas the protecting groups are benzyl, acetal, silyl and trityl or compromise F or methoxy groups instead of OH groups. According to specific embodiments, a furanosyl sugar or such analogs which are suitable for the synthesis of NAD or Nicotinamidmononucleosid and analogs thereof are used. In very specific embodiments, a furanosylamine is selected from the beta and alpha anomers of D and L ribose, xylose and arabinose.

Another suitable amine comprises cyclopentylamines which are the carba analogs of furanosylamines. In specific embodiments these analogs are selected from the group consisting of Beta-D-ribofuranosyl amines, -2-deoxyribofuranosylamine, or -2,3-dideoxy ribosylfuranosylamine the later preferably selected from (1R,2S,3R,4R)-2,3Dihydroxy-4-hydroxymethyl-1-aminocyclopentane, (1S,3R,4R)-3-Amino-4-hydroxy-cyclo-pentanemethanol, and (1R-cis)-3-amino-Cyclopentane-methanol.

In a further specific embodiment of a method according to the present disclosure, a Zincke-type salt is reacted with a primary amine (R6-NH2), wherein said primary amine is (1R,2S,3R,4R)-2,3Dihydroxy-4-hydroxymethyl-1 aminocyclopentane). Reacting an appropriate Zincke salt of the present disclosure with this primary amine leads to the formation of nicotinamido-carba riboside (3-Carbamoyl-1-((1R,2S,3R,4R)-2,3-dihydroxy-4-hydroxymethyl-cyclopentyl)-pyridinium chloride). Nicotinamido-carba riboside is a compound which is key to the synthesis of the carba analog to NAD. Carba-NAD and its preferred uses are described in detail in WO 2007/012494. The full disclosure of WO 2007/012494 is incorporated herein in its entirety by this reference.

Other substituted primary amines are selected from 3-Amino tetrahydrofuranes or protected 3-Amino-pyrollidines, e.g. (2R,4R)-4-Aminotetrahydrofuran-2-methanol (a heterocyclic analog of 2,3-dideoxyribosylamine) cyclohexylamines and Cyclohex-2-enyl amines, e.g. 6 ring sugar analogs as disclosed in Goulioukina, N. et al., Helvetica Chimica Acta 90 (2007) 1266-1278.

Examples of suitable phosphorylated amino sugars include (1R,4S,6S)-4-Amino-6-hydroxy-2-Cyclohexene-1-methanol-1-(dihydrogen phosphate), 2-Amino-1,5-anhydro-2-deoxy-6-(dihydrogen phosphate) D-Altritol, 2-Amino-1,5-anhydro-2,3-dideoxy- and 6-(dihydrogen phosphate) D-arabino-Hexitol.

As the skilled artisan will appreciate even compounds having an additional principally nucleophilic group in R6 can be used. In this case a further nucleophilic group has to be protected by an appropriate protecting group. Protecting groups are well known from the art and reviewed in standard text books (Greene, T., Protective groups in organic synthesis, John Wiley&Sons, Inc. (1981) New York, Chichester, Brisbane, Toronto). Preferably, amino groups are protected by boc-, phthaloyl- or trifluoracetyl-protecting groups, mercapto groups are protected as disulfide.

In an alternative embodiment the Zincke-type salt according to Formula I is used in a Zincke reaction with a compound having a free NH2 group. In this alternative embodiment R6 is selected from —OH, —NH2, —N(C1-C6alkyl)2, —NHC=Oaryl, —NHSO2aryl, —NHSO2-(C1-C6) alkyl, —NHC=O(C4-C13)-heteroaryl comprising one optionally substituted heteroatom selected from N, O, S or N—C1-C6 alkyl or protected N, —NHSO2-(C4-C13)-heteroaryl comprising one optionally substituted heteroatom selected from N, O, S or N—C1-C alkyl or protected N. In this embodiment Formula II represents a hydrazine, a hydroxylamine or a hydrazide. In this embodiment the following compounds may be used in a Zincke-type reaction: a) hydrazides; e.g. 2-(Pyridin-3-yl)acetohydrazide, 3-Indolylacetic acid hydrazide; 1,3-Benzodioxole-5-acetic acid hydrazide, 3-Phenylpropanoic acid hydrazide, Phenoxyacetic hydrazide, Cyclohexanecarboxylic hydrazide or Heptanoic acid hydrazide; Benzoic acid hydrazide; 4-Aminobenzoic acid hydrazide;

3-(Aminosulfonyl)-4-chloro-benzoic acid hydrazide; 4-Pyridinecarboxylic acid hydrazide; 3-Pyridinecarboxylic acid hydrazide; 2-Pyridinecarboxylic acid hydrazide; or acetic acid hydrazide, b) Sulfonic acid hydrazides, e.g., phenylsulfonic acid hydrazide, 4-Methoxybenzenesulfonic acid hydrazide; Methylsulfonic acid hydrazide, and c) hydrazines, e.g., 1-Amino-2-(methoxymethyl)pyrrolidine, 2-hydrazinylpyridine or 2 hydrazinyl isoquinoline.

In another specific embodiment 4,4'-bipyridines are reacted with two equivalents of an electron deficient heteroaromate to produce an N,N'-bisheteroaryl bispyridinium salt. Such "bis Zincke salts" can be reacted with amines to form N,N' bisubstituted bipyridines, which are known as viologens. Viologens exhibit very interesting electrochemical properties. Synthesis of viologens is described by Inagaki, Y. et al., Journal of Materials Chemistry 16 (2006) 345-347; Liu, Y. et al., Organic Letters 10 (2008) 765-768, incorporated herein by this reference.

If the N,N'-bisheteroaryl bispyridinium salts are reacted with bisamines, polyviologens will result, which have a broad range of applications as electrochromic materials or as semiconductors. In a further embodiment the present disclosure thus relates to method for producing a polyviologen by reacting a N,N'-bisheteroaryl bispyridinium salt with a bisamine.

As appreciated from the above examples, many different compounds according to Formula II are compatible with the Zincke reaction.

The novel procedures presently disclosed have several advantages compared to the standard procedure with respect to 2,4-Dinitrophenyl Zincke salts. Aromatic heterocycles like 2-amino-6-chloro purine or 2-chloro-4,6-dimethoxy triazine are cheap and readily available. They are non-explosive compounds and therefore the Zincke salt formations and Zincke reaction can easily be scaled up without any undue precautionary measures.

The following examples are provided to aid the understanding of the present disclosure, the true scope of which is set forth in the appended claims. It is understood that modifications can be made in the procedures set forth without departing from the spirit of the disclosure. The examples are provided for the purpose of demonstrating various embodiments of the instant disclosure and aiding in an understanding of the present disclosure. These examples are not intended to, and should not be understood as, limiting the scope or spirit of the instant disclosure in any way.

EXAMPLES

Example 1

1-(2 amino-purin-6yl) 3 carboxamidopyridinium chloride

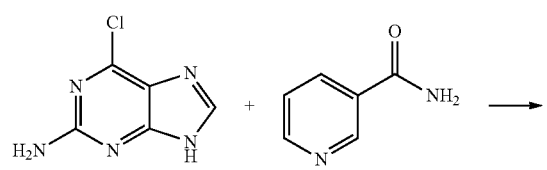

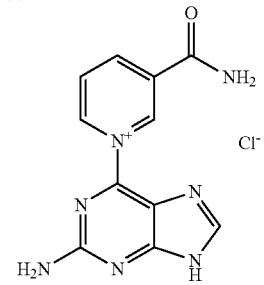

967 g (5.7 mol) 2-Amino-6-chlorpurin (Carbosynth Batch FA025810801) and 562 g (4.6 mol) Nicotinamide (Fluka 72340) were heated in 5 l dimethylformamide for 7 h under stirring at 95-97° C. The mixture was stored at room temperature overnight. The mixture was filtrated and the residue was suspended in 3 l acetone; the suspension was stirred for 1 h at room temp. The mixture was filtrated and the residue was dried for 2 days in vacuum.

Yield 1200 g

TLC (HPTLC-Diol Plates, Merck-Nr. 1.12668.0001) 1-butanol/acetic acid/water 10/3/5, Rf=0.41

Using 2-amino-6-chloro-pyridine as heteroaromatic compound in reaction with nicotine amide can easily be performed in DMF at 100° C. or even below. The product simply precipitates after cooling to room temperature and could be easily separated by filtration. The Zincke reaction of the resulting Zincke salt with (1R,2S,3R,4R)-2,3Dihydroxy-4-hydroxymethyl-1 aminocyclopentane was performed in an polar solvent (see Example 2).

The resulting "by-product" 2,6diaminopurine is easily removed by adjusting the pH and subsequent filtration.

Example 2

3-Carbomoyl-1-((1R,2S,3R,4R)-2,3-dihydroxy-4-hydroxymethyl-cyclopentyl)-pyridinium; chloride

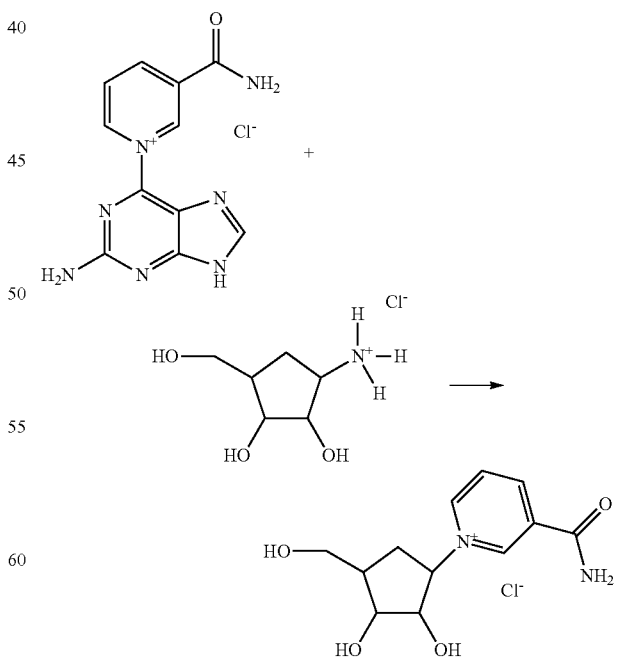

537 g (2.93 mol) (1R,2S,3R,4R)-2,3-dihydroxy-hydroxymethyl-1-amino-cyclopentanhydrochlorid (Chirotec 004-003), 900 g (3.09 mol) 1-(2 amino-purin-6-yl)3 carboxamidopyridinium chloride ("Purine Zincke salt") and 1.1 L (9.1 mol) N-ethyldiisopropylamine (Fluka 03440) were given to 7.5 L Methanol. The mixture was heated under stirring to 60° C. for 2 h. After cooling to room temperature the mixture was filtrated by using a Seitz filter.

The filtrate was evaporated by using a rotary evaporator and the resulting residue was dissolved in 7.5 L water. After adjusting to pH 4.2 with 2 M HCl a yellow precipitate formed. The mixture was stored overnight at 4° C., filtrated and to the filtrate were added activated charcoal. After stirring for 30 min at room temp the mixture was filtrated using a Seitz filter. The slightly yellow filtrate was evaporated by using a rotary evaporator, yielding 800 g of an orange oil, which was pure enough for further reactions.

For further purification, the residue can be dissolved in methanol and precipitated with ethyl acetate.

TLC: (HPTLC-Diol plates, Merck-Nr. 1.12668.0001) 1-butanol/acetic acid/water 10/3/5 Rf=0.39.

This crude product is suitable for synthesis of a NAD analog as shown in Examples 5 and 6.

Higher purities were obtained by ion exchange chromatography using a cation exchanger and eluting with water.

Example 3

1-(4,6 dimethoxy-traizine-2 yl)carboxamidopyridium chloride

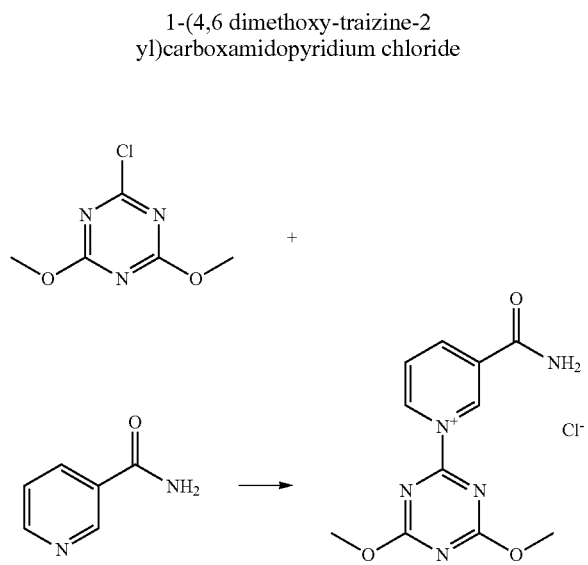

9.2 g (51.5 mol) 2 chloro 4.6 dimethoxy triazine and 6.2 g (5.0 mol) Nicotinamide (Fluka 72340) were heated in 40 ml dimethylformamide for 0.5 h under stirring at 80° C. The mixture was stored at room temperature for 2 h. The mixture was filtrated and the residue was washed two times with acetone. The product was dried for 2 days in vacuum.

Yield 12, 4 g

Using 2-chloro-4,6-dimethoxy triazine as heteroaromatic compound in the reaction with nicotine amide the reaction can be performed in DMF at far below 100° C., e.g. at 80° C. as shown above. The product precipitates after cooling to room temperature and thus could be easily separated by filtration. The Zincke reaction of the resulting Zincke salt with (1R,2S,3R,4R)-2,3Dihydroxy-4-hydroxymethyl-1aminocyclopentane was performed in an polar solvent (see Example 4).

Example 4

3-Carbamoyl-1-((1R,2S,3R,4R)-2,3-dihydroxy-4-hydroxymethyl-cyclopentyl)-pyridinium; chloride 1.6 g (8.5 mmol) (1R,2S,3R,4R)-2,3-dihydroxy-hydroxymethyl-1-amino-cyclopentanhydrochlorid (Chirotec 004-003), 3.4 g (10 mmol) 1-(4,6-dimethoxy-traizine-2yl) 3 carboxamidopyridinium chloride ("Triazine Zincke salt") and 3.2 ml N-ethyldiisopropylamine (Fluka 03440) were given into 50 ml Methanol. The mixture was heated under stirring to 60° C. for 2 h. After cooling to room temperature the mixture was filtrated by using a D4-frit.

The filtrate was evaporated by using a rotary evaporator and the resulting residue was dissolved in 30 ml Methanol. and dropped under vigorous stirring in 250 ml ethyl acetate. The mixture was stored at one hour at room temp. The supernatant was removed by decantation. The crude product was dried under vacuum (1 mbar).

Example 5

Conversion of 3-Carbamoyl-1-((1R,2S,3R,4R)-2,3-dihydroxy-4-hydroxymethyl-cyclopentyl)-pyridinium; chloride to carba nicotinamide 1 g (2.16 mmol) of 3-Carbamoyl-1-((1R,2S,3R,4R)-2,3-dihydroxy-4-hydroxymethyl-cyclopentyl)-pyridinium; chloride, 0.242 g (0.4 mmol) ATP di sodium salt, 300 mg MgCl2× 6H2O (1.45 mmol) 16 U Ribosylkinase, 1.45 g (4.43 mmol) creatinphosphate and 4.27 kU creatinkinase were dissolved in 25 ml sterile water. The mixture was incubated at 35° C. overnight. Then 2.42 g (4 mmol) ATP di sodium salt, 440 mg MgCl2×6H2O (2.16 mmol) and 32 U nicotine amide mononucleotide adenosyl transferase (NMN-AT) were added. The mixture was incubated at 35° C. overnight. Then it was heated to 90° C. for 5 min and after cooling filtrated. Purification was performed by using ion exchange chromatography as described in WO 2007/012494.

For 3-Carbamoyl-1-((1R,2S,3R,4R)-2,3-dihydroxy-4-hydroxymethyl-cyclopentyl)-pyridinium; chloride as e.g. obtained in Examples 2 or 4, respectively, the correct mass of carba NAD was found in HPLC MS/ESI negative mode.

Example 6

1-(2 amino-purin-6yl) 3 thiocarboxamidopyridinium chloride and 3-Thiocarbamoyl-1-((1R,2S,3R,4R)-2, 3-dihydroxy-4-hydroxymethyl-cyclopentyl)-pyridinium; chloride

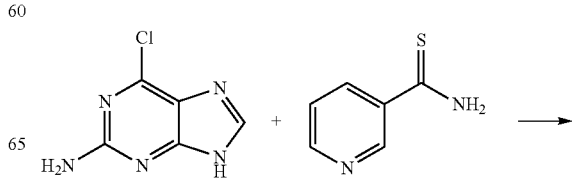

17

-continued

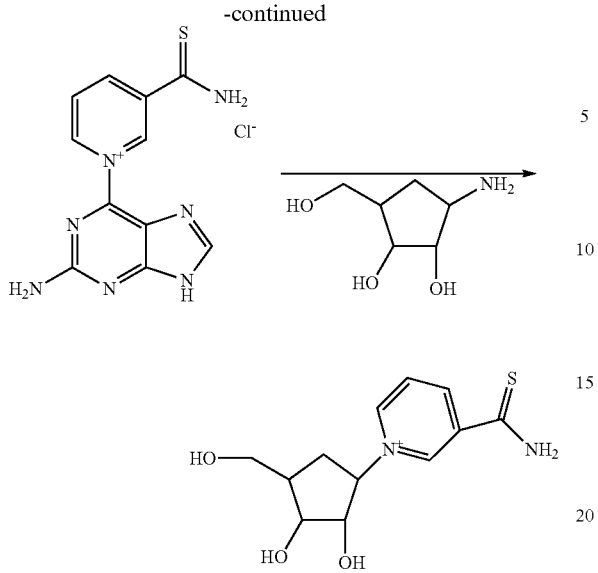

Using the same method as described in Example 1 thionicotinamide could be converted to 1-(2 amino-purin-6-yl) 3 thiocarboxamidopyridinium chloride, which is then converted to 3-thiocarbamoyl-1-((1R,2S,3R,4R)-2,3-dihydroxy-4-hydroxymethyl-cyclopentyl)-pyridinium; chloride by the method described in Example 2.

Example 7

Other Aromatic Heterocycles for Formation of Zincke-Type Salts

Using an analogous method as described in Example 1 and Example 3, respectively, different aromatic heterocycles were tested in combination with nicotinamide in order to obtain a Zincke salt appropriate for use in a method according to the present disclosure. 2-amino-4-chloro-pyrimidine and 1,4-dichloro-6,7dimethoxyquinazoline also could be converted into the a Zincke salt according to the disclosure and these Zincke salts could thereafter be reacted to the 3-Carbamoyl-1-((1R,2S,3R,4R)-2,3-dihydroxy-4-hydroxymethyl-cyclopentyl)-pyridinium; chloride in analogy to the methods shown in Examples 2 and 4.

All publications, patents and applications are herein incorporated by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method for synthesis of an N-substituted pyridinium compound comprising the steps of:

18 a) providing a Zincke salt according to any of following Formulas (IV)-(VII) and having at least one counter ion, selected from the group consisting of: Cl, Br, Tosylate, Mesylate, and Triflate:

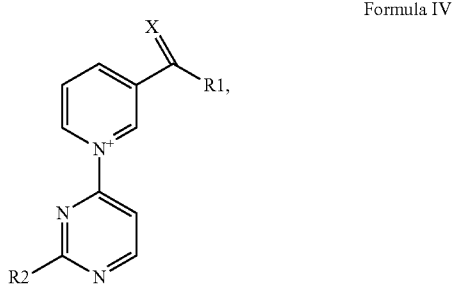

Formula IV wherein
X is O or S,
R1 is methyl, ethyl, O-methyl, O-ethyl, $NH_2$, N-dimethyl, N-diethyl, and
R2 is $NH_2$;

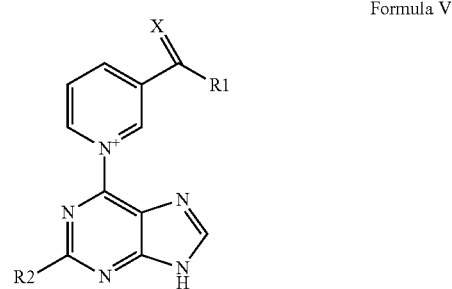

Formula V wherein
X is O or S,
R1 is methyl, ethyl, O-methyl, O-ethyl, $NH_2$, N-dimethyl, N-diethyl, and
R2 is $NH_2$ or Cl;

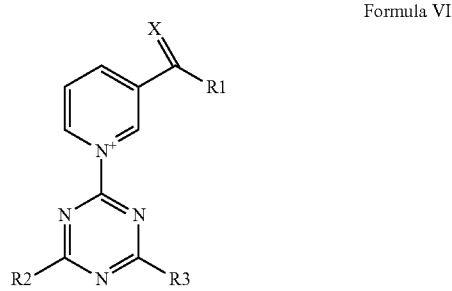

Formula VI wherein
X is O or S,
R1 is methyl, ethyl, O-methyl, O-ethyl, $NH_2$, N-dimethyl, N-diethyl, and
R2 and R3 independently are O—C1-C3 alkyl or $NH_2$;

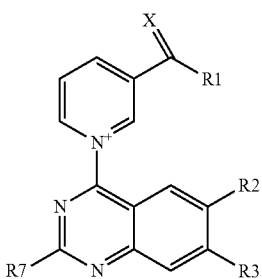

Formula VII wherein
X is O or S,
R1 is methyl, ethyl, O-methyl, O-ethyl, NH$_2$, N-dimethyl, N-diethyl, and
R2 and R3 independently are O—C1-C3 alkyl and R7=H or Cl;

b) reacting the Zincke salt of step (a) with a primary amine of Formula II:

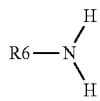

Formula II wherein
the primary amine of Formula II is selected from the group consisting of: an alkyl amine, an alkyenyl amine, a heterocycloalkyl amine, an aryl amine, a heteroaryl amine, an amino alcohol, an amino acid, a furanoxylamine, or a cyclopentylamine, c) obtaining, an N-substituted pyridinium compound of Formula III:

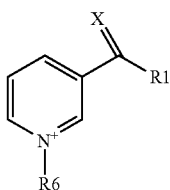

Formula (III)

having a counter ion,
wherein X is O or S,
R1, is methyl, ethyl, O-methyl, O-ethyl, NH$_2$, N-dimethyl, N-diethyl; and R6 is selected from the group consisting of: alkyl, alkyenyl, heterocycloalkyl, aryl, heteroaryl, hydroxyalkyl, carboxylic acid, a furanoxyl, or cyclopentyl.

2. The method according to claim 1, wherein the primary amine according to Formula II is (1R,2S,3R,4R)-2,3 Dihydroxy-4-hydroxymethyl-1 aminocyclopentane.

3. The method according to claim 1, wherein the primary amine according to Formula II is 3-amino-5-hydroxymethyl-cyclopentane-1,2-diol.

4. The method of claim 1, wherein the Zincke salt is selected from the group consisting of: 1-(2 amino-purin-6-yl) 3 carboxamidopyridinium chloride, 1-(4,6 dimethoxy-traizine-2 yl) 3 carboxamidopyridinium chloride, and 1-(2 amino-purin-6-yl) 3 thiocarboxamidopyridinium chloride.

5. The method of claim 1, wherein R6 is selected from the group consisting of a linear or branched $C_1$-$C_{20}$ alkyl; a mono-, bi-, or tricylo $C_3$-$C_{10}$ alkyl; a linear or branched $C_3$-$C_{20}$ alkenyl; a mono-, bi-, or tricycle $C_5$-$C_{10}$ alken-1-yl, a linear or a branched $C_3$-$C_{20}$ alkinyl, a $C_5$-$C_6$ cycloalkyl, an optionally substituted heteroatom selected from the groups consisting of O, NC$_1$-C$_3$ alkyl, and a protected N; $C_6$-$C_{14}$ aryl; a Y—$C_4$-$C_{13}$ heteroaryl wherein Y is selected from the group consisting of: N, O, S, or a N—$C_1$-$C_6$ alkyl, wherein the protected N is substituted with either a tosyl or boc protecting group.

6. The method of claim 1, wherein R6 is a cycloalkane.

7. The method of claim 1, wherein R6 is selected from the group consisting of —OH, —NH$_2$, —N(C$_1$-C$_6$ alkyl)$_2$, —NHC═Oaryl, —NHSO$_2$aryl, —NHSO$_2$—(C$_1$-C$_6$ alkyl), —NHC═Oheteroaryl of the formula (Y—C$_3$-C$_{14}$), wherein Y is selected from the group consisting of: N, O, S, or N—(C$_1$-C$_6$) alkyl, protected N, —NHSO$_2$, C$_4$-C$_{13}$, protected N is substituted with a tosyl- or boc-protecting group.

8. The method of claim 1, wherein the Zincke salt is a Zincke salt according to Formula V, wherein R1 is NH$_2$.

9. The method of claim 1, wherein X is O.

10. The method of claim 1, wherein X is S.

11. The method of claim 1, further comprising the steps of: mixing 2-amino-4-chloro-pyrimidine and nicotinamide stirring said mixture of 2-amino-4-chloro-pyrimidine and nicotinamide for about 7 hours at 95-97C;
cooling said mixture to room temperature; and
suspending said mixture in an inert organic solvent; and
filtering said suspension to recover the Zincke salt rich residue.

12. The method of claim 1, wherein Formula III is 3-Carbamoyl-1-((1R,2S,3R,4R)-2,3-dihydroxy-4-hydroxymethyl-cylopentyl)pyridinium chloride.

* * * * *